(12) United States Patent
Nativ et al.

(10) Patent No.: US 10,390,834 B2
(45) Date of Patent: Aug. 27, 2019

(54) CIRCULAR SURGICAL STAPLERS WITH ISOLATING SLEEVES STORED INSIDE ANVIL

(71) Applicant: Ethicon, LLC, San Lorenzo, PR (US)

(72) Inventors: Nir I. Nativ, West Orange, NJ (US); Silvia Chen, Hillsborough, NJ (US)

(73) Assignee: Ethicon LLC, San Lorenzo, PR (US)

( * ) Notice: Subject to any disclaimer, the term of this patent is extended or adjusted under 35 U.S.C. 154(b) by 367 days.

(21) Appl. No.: 15/277,470

(22) Filed: Sep. 27, 2016

(65) Prior Publication Data

US 2018/0085125 A1    Mar. 29, 2018

(51) Int. Cl.
| | |
|---|---|
| *A61B 17/03* | (2006.01) |
| *A61B 17/12* | (2006.01) |
| *A61B 17/064* | (2006.01) |
| *A61B 17/115* | (2006.01) |
| *A61B 17/11* | (2006.01) |
| *A61B 17/072* | (2006.01) |
| *A61B 17/00* | (2006.01) |

(52) U.S. Cl.
CPC ....... *A61B 17/1155* (2013.01); *A61B 17/1114* (2013.01); *A61B 17/07292* (2013.01); *A61B 2017/00884* (2013.01); *A61B 2017/00889* (2013.01); *A61B 2017/00893* (2013.01); *A61B 2017/07257* (2013.01); *A61B 2017/1132* (2013.01)

(58) Field of Classification Search
CPC ...... A61B 2017/07257; A61B 17/1155; A61B 17/07292
USPC ........................................ 606/154, 153, 151
See application file for complete search history.

(56) References Cited

U.S. PATENT DOCUMENTS

| | | | |
|---|---|---|---|
| 5,250,058 A | 10/1993 | Miller et al. | |
| 5,271,544 A | 12/1993 | Fox et al. | |
| 7,527,185 B2 | 5/2009 | Harari et al. | |
| 7,776,060 B2 * | 8/2010 | Mooradian | A61B 17/115 |
| | | | 227/180.1 |

(Continued)

FOREIGN PATENT DOCUMENTS

| EP | 1588667 | 10/2006 |
|---|---|---|
| WO | WO 1997/31575 | 9/1997 |

OTHER PUBLICATIONS

International Search Report re: PCT/US2017/051953 dated Nov. 7, 2017.

(Continued)

*Primary Examiner* — Andrew M Tecco
*Assistant Examiner* — Eyamindae C Jallow
(74) *Attorney, Agent, or Firm* — David R. Crichton; Leo B. Kriksunov

(57) ABSTRACT

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage. The present invention further relates to circular stapling instruments and elongated tubular hollow sleeves deployed from such stapling instruments and establishing an enclosure around the stapled and resected tissues at the anastomotic joint.

19 Claims, 16 Drawing Sheets

(56) References Cited

U.S. PATENT DOCUMENTS

| | | |
|---|---|---|
| 7,776,081 B2 | 8/2010 | Zuidema et al. |
| 7,793,813 B2 * | 9/2010 | Bettuchi .......... A61B 17/07292 |
| | | 227/179.1 |
| 7,886,951 B2 * | 2/2011 | Hessler ................ A61B 17/115 |
| | | 227/175.1 |
| 8,167,895 B2 | 5/2012 | D'Agostino et al. |
| 8,257,391 B2 | 9/2012 | Orban, III et al. |
| 8,286,849 B2 | 10/2012 | Bettuchi |
| 8,372,094 B2 * | 2/2013 | Bettuchi .............. A61B 17/072 |
| | | 606/153 |
| 8,511,533 B2 | 8/2013 | Viola et al. |
| 8,821,523 B2 | 9/2014 | Heinrich et al. |
| 9,010,605 B2 | 4/2015 | Olson et al. |
| 9,248,038 B2 * | 2/2016 | Stack ................ A61B 17/0469 |
| 2003/0183671 A1 * | 10/2003 | Mooradian .......... A61B 17/115 |
| | | 227/175.1 |
| 2005/0228446 A1 | 10/2005 | Mooradian et al. |
| 2006/0271104 A1 * | 11/2006 | Viola ............... A61B 17/00491 |
| | | 606/214 |
| 2008/0290134 A1 * | 11/2008 | Bettuchi .......... A61B 17/07207 |
| | | 227/176.1 |
| 2009/0076510 A1 * | 3/2009 | Bell ................. A61B 17/07207 |
| | | 606/75 |
| 2012/0241492 A1 | 9/2012 | Shelton, IV et al. |
| 2014/0358167 A1 | 12/2014 | Armstrong |
| 2015/0351764 A1 * | 12/2015 | Shelton, IV ..... A61B 17/00491 |
| | | 227/176.1 |

OTHER PUBLICATIONS

Written Opinion re: PCT/US2017/051953 dated Nov. 7, 2017.

Ho, Y.H. et al "Techniques for colorectal anastomosis", World Journal of Gastroenterology (2010) 16(13), pp. 1610-1621.

Jönsson, K. et al "Breaking strength of small intestinal anastomoses" The American Journal of Surgery (1983) v. 145, pp. 800-803.

Morks, A.N. et al "The C-seal: A Biofragmentable Drain Protecting the Stapled Colorectal Anastomosis from Leakage" (2010) J. Vis. Exp. (45), p. 2223.

* cited by examiner

FIG. 2A
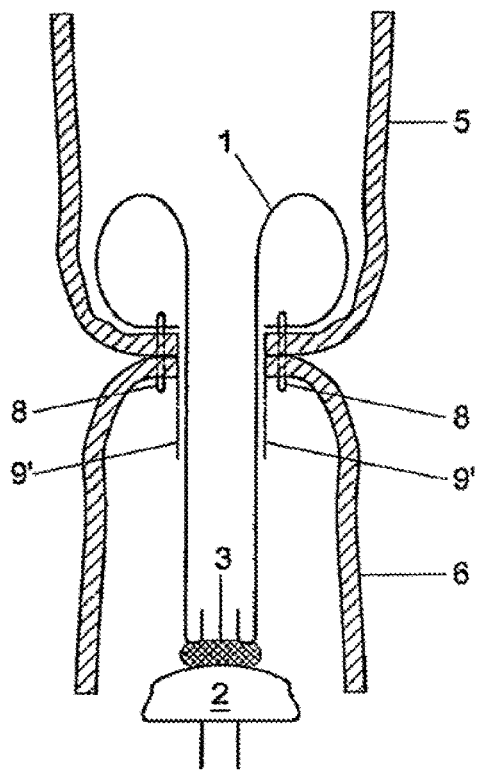
FIG. 2 B
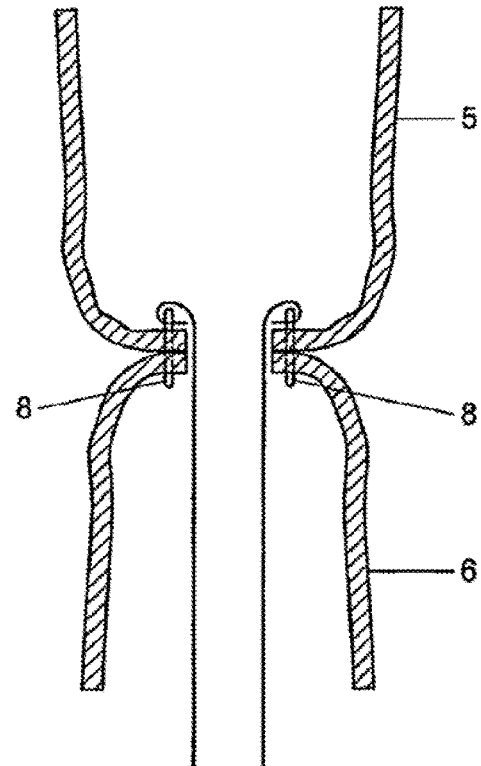
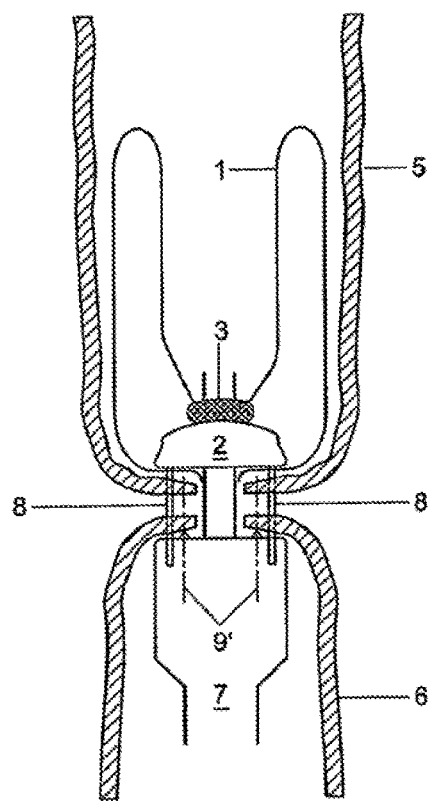
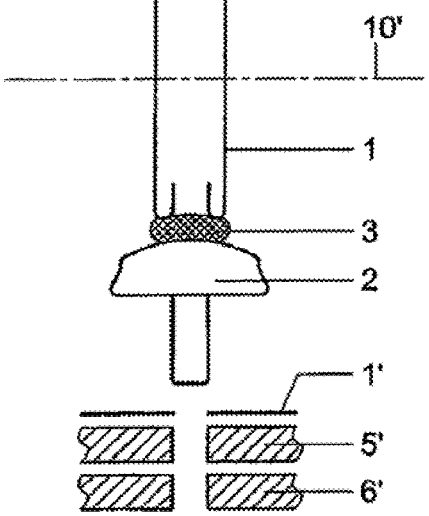
FIG. 2C

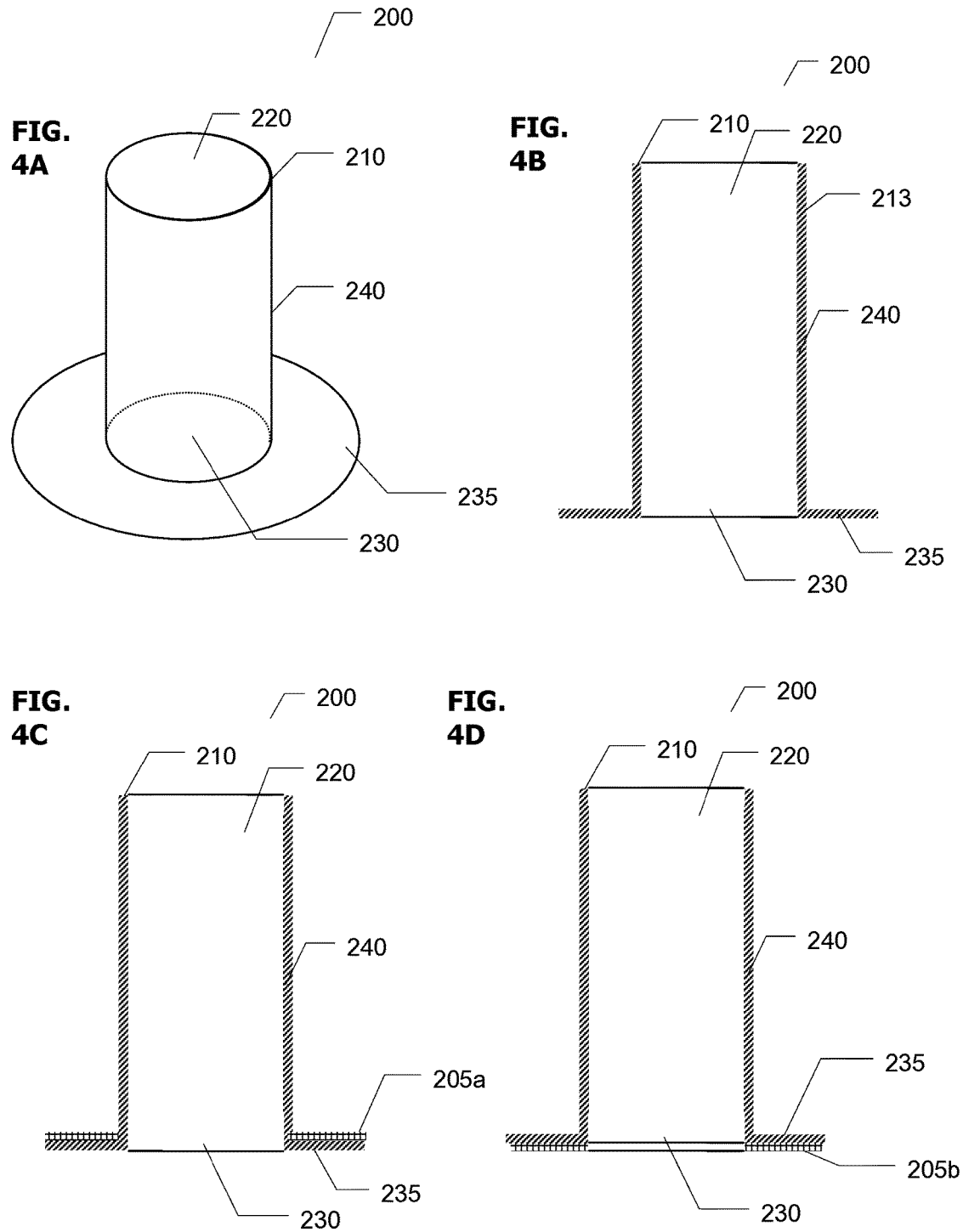

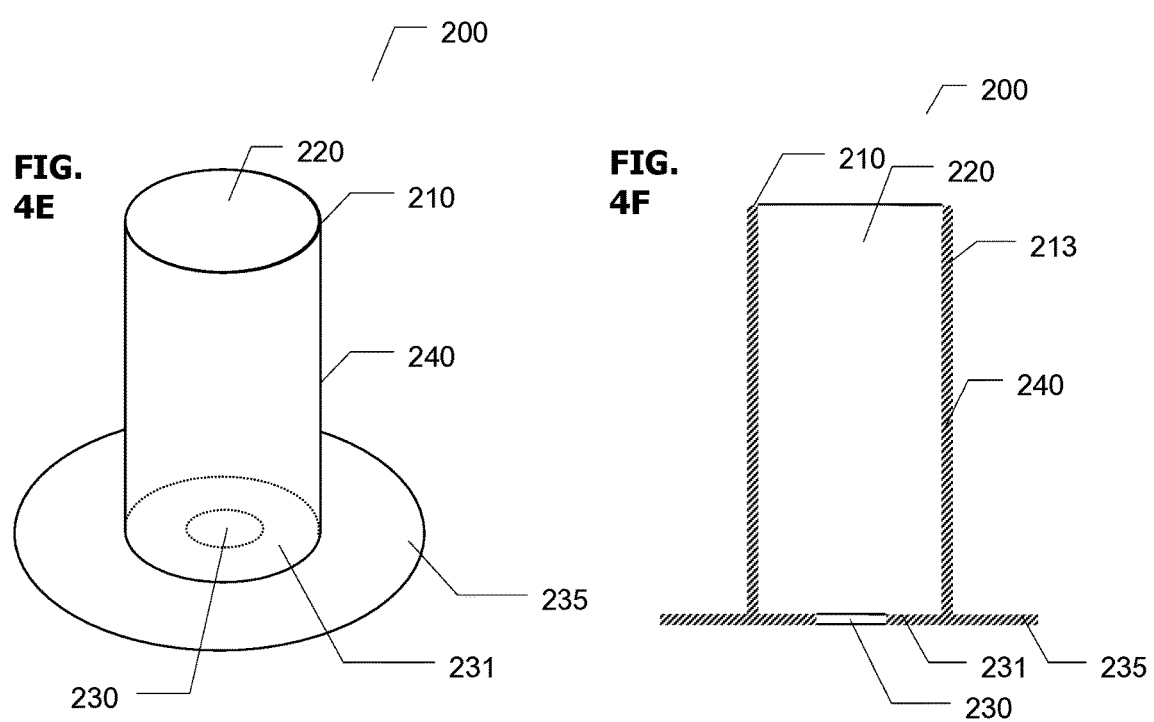

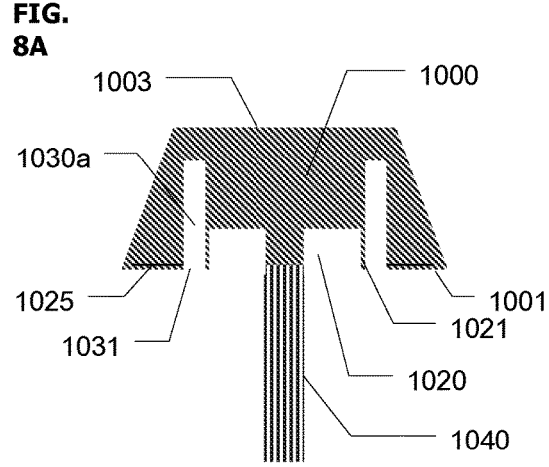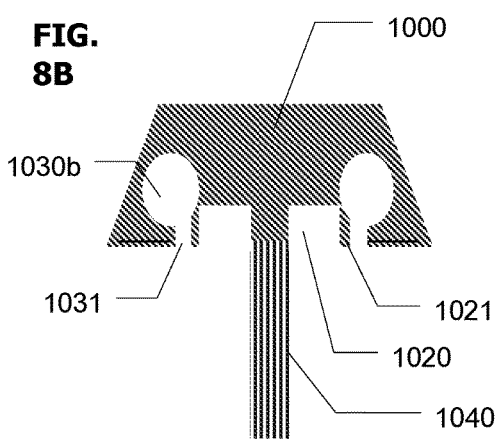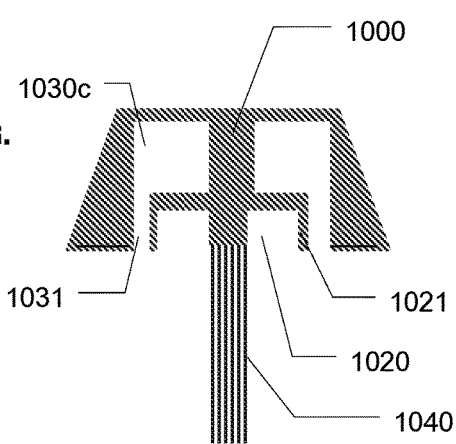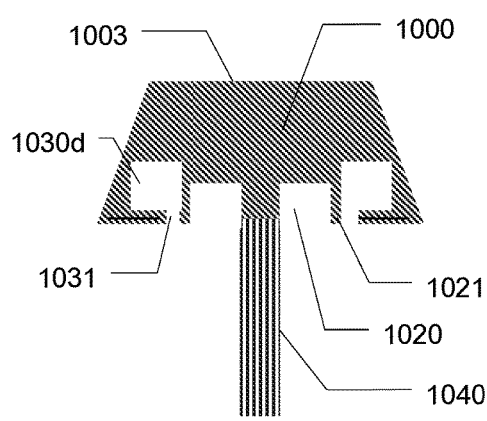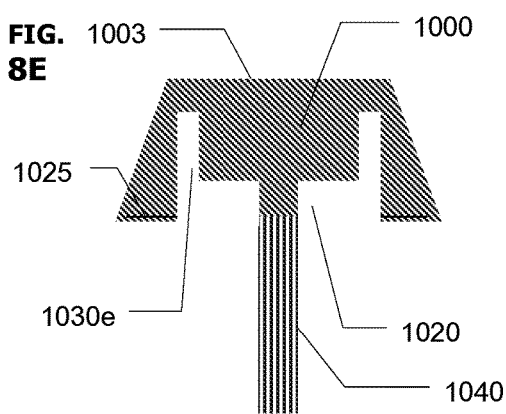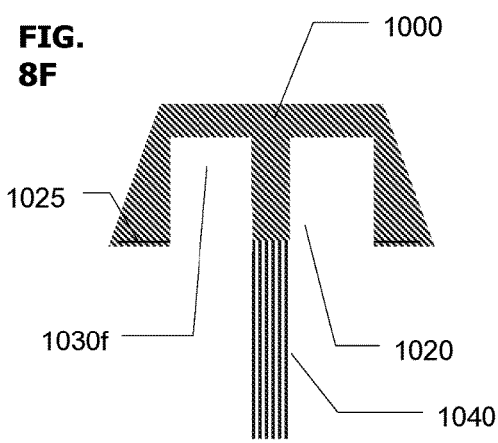

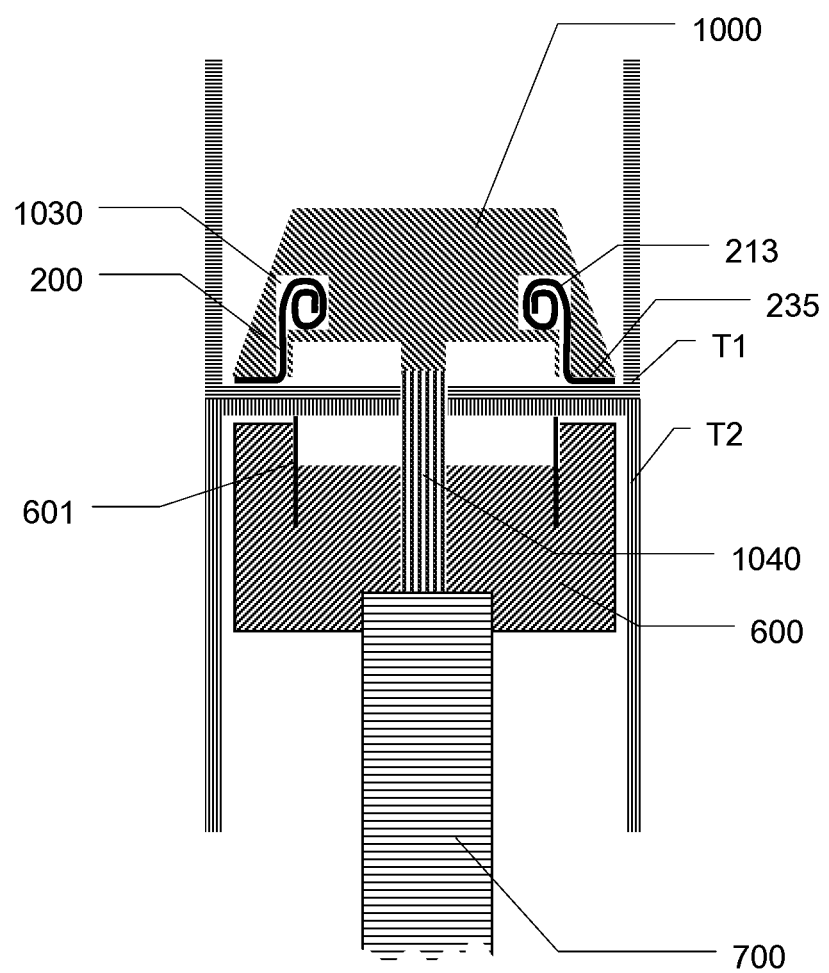

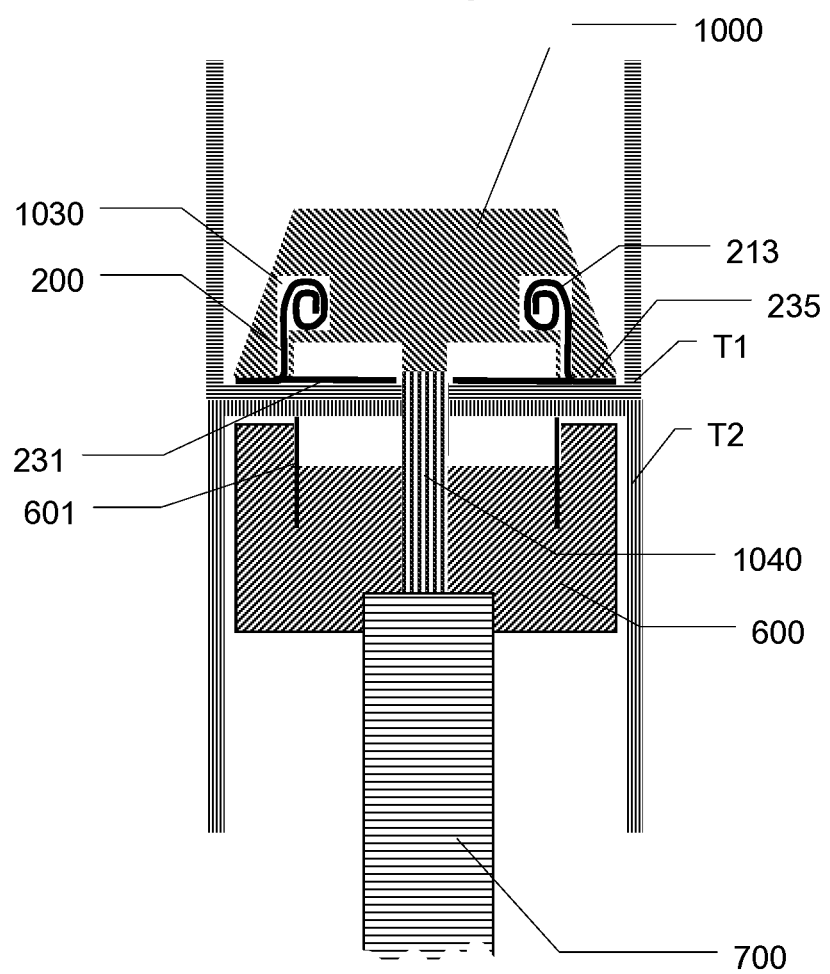

CIRCULAR SURGICAL STAPLERS WITH ISOLATING SLEEVES STORED INSIDE ANVIL

FIELD OF THE INVENTION

The present invention relates to surgical instruments and methods for enhancing properties of tissue repaired or joined by surgical staples and, more particularly to surgical instruments and methods designed to reinforce and isolate the repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular/circular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular or circular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis in a separate step.

U.S. Pat. No. 7,776,081 entitled "Devices and methods for anastomosis" by Johan Zuidema et al. discloses a method of treating a human or animal organism comprising inserting a tube formed from a biocompatible, biodegradable polymer into a lumen at a point of a desired anastomosis, joining two ends of biological vessels together to create an anastomosis, and with one end of the tube being firmly attached to a proximal end of the anastomosis, inverting the tube by drawing the other end of the tube through the anastomosis and extending through the anastomosis such that the tube allows natural contents of the lumen to drain through and with the tube shielding the anastomosis in the organism from the natural contents of the lumen.

An article entitled "The C-seal: A Biofragmentable Drain Protecting the Stapled Colorectal Anastomosis from Leakage", by A. N. Morks et al., published in J. Vis. Exp. (45), p. 2223 (2010), discloses so called C-seal which is a biofragmentable drain, which is stapled to the anastomosis with the circular stapler.

U.S. Patent Publication 2014/0358167 "ANASTOMOTIC SLEEVE DEVICE" discloses a system for performing a medical procedure comprising: a) a stapler comprising: a detachable anvil head comprising an anvil surface and a hollow rod comprising a lumen protruding from the anvil surface, a stapler shaft comprising a stapler surface and a spike protruding from the stapler surface, and a shape cutter, wherein the anvil surface comprises a groove, wherein the stapler surface comprises a staple port and a cutter port wherein the cutter can advance through the cutter port, and wherein the spike is proportioned to fit inside the lumen of the hollow rod; and b) a support structure comprising: a first shield piece comprising a first support surface and at least one first wall comprising a first bottom edge wherein the first bottom edge is attached to the first support surface and a second shield piece comprising a second support surface, wherein the second shield piece is not attached to the first shield piece, wherein the first support surface and/or the second support surface comprises a hole, and wherein the first support surface and the second support surface align with the anvil surface and the stapler surface to provide for the delivery of a staple through the first support surface and the second support surface.

Various compression anastomotic ring systems have been pursued as a replacement to the staple-based anastomotic closure. For example, LARA™ compression anastomotic ring system developed by novoGI™ utilizes nitinol-based compression ring specifically targeting low anterior resection (LAR) procedures.

U.S. Pat. No. 7,527,185 "Compression anastomosis ring assembly and applicator for use therewith" assigned to Niti Surgical Solutions Ltd., discloses a compression anastomosis ring (CAR) assembly which comprises: a first portion which comprises: an anvil ring; and a second portion which comprises: a bottom ring positioned substantially parallel to and spaced apart from said anvil ring, said anvil ring and said bottom ring being adapted to be brought together in the presence of a closure force applied thereacross: at least one ring element, where one of said at least one ring elements is a needle ring positioned on a side of said bottom ring distal from said anvil ring, said needle ring having a plurality of needles extending generally transversely therefrom toward said first portion; and at least one spring element which provides a restorative force formed at least partially of a shape-memory alloy, said spring element positioned on one of said at least one ring elements and being in compressive force transmissive contact with said bottom ring, and wherein when said compression anastomosis ring (CAR) assembly is positioned so as to hold between said anvil ring and said bottom ring tissue portions to be compressed and joined by anastomosis, said needle ring is operative, in response to the closure force to drive said plurality of needles through the tissue portions to be compressed and to anchor said plurality of needles in said anvil ring, and wherein when said anvil ring and said bottom ring are brought together in the presence of the closure force holding the tissue portions therebetween, and when said anvil ring is anchored by said plurality of needles, the restorative force provided by said at least one spring element is operative on said bottom ring to compress said tissue portions thereby effecting anastomosis.

U.S. Pat. No. 5,250,058 "Absorbable anastomosic fastener means" assigned to ETHICON INC., discloses a mechanism which is capable of anastomosis of two lumens by an absorbable fastener. The fastener is made from two washer-like plates. One such plate has holes to receive latching prongs protruding from the other plate. Fastening is done through a single linear motion that causes the prongs to pierce the tissue, latches the prongs into a receiver and causes a knife blade to cut through excess fastener material and tissue. The ease of removal, by pulling the mechanism through the formed anastomosis, is greatly enhanced. The system can be used such that the plates can be placed in any configuration to properly anastomose tissue. The patent discloses a compression anastomosis device comprising: a piercing ring containing a plurality of piercing flanges; a receiving ring containing a plurality of receiving slots corresponding to said flanges; and spring means placed between said piercing and receiving rings to exert a spring force on one of said piercing and receiving rings.

Post-operative leakage of the stapled tissue seals, including anastomotic seals has been shown to lead to morbidity and mortality. A number of technologies are related to direct application of material to the serosal layer after stapling by either dripping or spraying. The problems associated with these techniques are that access is very difficult and visual assessment as to whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, assuming the material was applied to the correct spot intraoperatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult.

U.S. Pat. No. 8,511,533 "Annular adhesive structure" discloses a surgical stapling device for joining tissue portions, comprising: a handle assembly; an anvil assembly at a distal end of the stapling device, the anvil assembly having a shaft for removably connecting the anvil assembly to the stapling device; a tubular body portion, the tubular body portion having a staple cartridge assembly containing a plurality of surgical staples in an annular array, the anvil assembly and tubular body portion being juxtaposed with respect to one another along the shaft and arranged so as to be approximated with respect to one another; and an applicator supported on the shaft of the anvil assembly, the applicator having a disc-shaped structure disposed between the anvil member and tubular body portion, the disc-shaped structure having a channel radially oriented and open at lateral sides of the disc-shaped structure, the channel being arranged for dispensing a wound treatment material.

U.S. Pat. No. 8,372,094 "Seal element for anastomosis" discloses an assembly for disposing a seal element between tissue lumens comprising: a circular surgical stapling device comprising an anvil assembly and a tubular body portion wherein the anvil assembly comprises an anvil member and a first shaft and the tubular body portion comprises a plurality of surgical staples in a circular configuration and a second shaft disposed inwardly of the surgical staples, the first shaft being attachable to the second shaft; and a seal element disposable between tissue lumens, the seal element comprising a first material and a second material wherein the first material promotes tissue ingrowth and the second material comprises a sealant.

U.S. Pat. No. 8,286,849 "Hub for positioning annular structure on a surgical device" discloses an assembly for disposing an annular structure between adjacent intestinal sections, the assembly comprising: an annular surgical stapling device having an anvil assembly and a tubular body portion, the anvil assembly having an anvil member and an anvil shaft, the tubular body portion carrying a plurality of surgical staples in an annular configuration, the tubular body portion having a connection member disposed radially inward of the surgical staples, the anvil shaft of the anvil member including a flange and being attachable to the connection member of the tubular body portion; and a hub adapted for support on the anvil shaft to engage the flange of the anvil shaft, the hub selectively receiving the anvil shaft therein, and an annular structure radially extending from the hub, the hub including a plurality of resilient fingers extending substantially in a longitudinal direction and arranged to engage the flange of the anvil shaft to position the annular structure at a location spaced a distance from a tissue contacting surface of the anvil assembly and the tubular body portion, wherein the annular structure comprises a material selected from the group consisting of: an adhesive, a sealant, a hemostat, and a medicament.

U.S. Pat. No. 8,257,391 "Annular support structures" discloses a system for joining a first body tissue and a second body tissue, the system comprising: a circular endoscopic stapling instrument having a staple cartridge assembly and an anvil assembly for approximating and joining a first body tissue to a second body tissue, and an elongated shaft extending between the staple cartridge assembly and the anvil assembly; and a reinforcing support structure supported on the shaft of the stapling instrument at a location spaced a distance from the anvil assembly and spaced a distance from the staple cartridge assembly, the reinforcing support structure having a central hub for connection to the shaft of the stapling instrument and at least one annular reinforcing ring supported on the central hub so that the at least one annular reinforcing ring is supported on the shaft at a location between the first body tissue and the second body tissue, wherein the at least one annular reinforcing ring includes a radial outer ring and a radial inner ring, the reinforcing support structure including at least one support spoke integrally extending between the radial inner ring and the central hub, and wherein, after firing of the stapling instrument, the at least one annular reinforcing ring is interposed between and reinforces the joined first body tissue and the second body tissue.

U.S. Pat. No. 8,167,895 "Anastomosis composite gasket" discloses a method of forming an anastomosis between intestinal tissue sections, comprising the steps of: providing a circular surgical anastomosis device, the circular surgical anastomosis device including: an anvil assembly having an anvil member; and a tubular body portion having an annular knife operatively disposed therein and a shaft disposed radially inward of the annular knife, the anvil assembly being attached to the shaft of the tubular body; inserting the anvil assembly into a first intestinal section; inserting the tubular body portion into a second intestinal section; disposing a structure, including at least a first ring of a first material, a second ring of a second material, and a third ring between the first intestinal section and the second intestinal section, the first ring comprising a disk having an aperture and the second ring comprising a disk having an aperture, the second ring having an outer perimeter, wherein the outer perimeter of the second ring is directly attached to the first ring and disposed within the aperture of the first ring, and the third ring radially extending outward from the first ring and beyond staple retaining slots of the tubular body portion, the structure possessing a wound treatment material consisting of at least one of an adhesive and a sealant; and firing staples through the intestinal tissue sections and through the structure.

U.S. Pat. No. 7,886,951 "Pouch used to deliver medication when ruptured" discloses an anvil assembly for a circular stapling device, the anvil assembly comprising: an anvil head configured to support an anvil plate thereon; a shaft extending from the anvil head and configured to selectively engage a rod member of the circular stapling device; an anvil plate operatively connected to the anvil head, wherein the anvil plate includes an inner diametral edge, and wherein the anvil plate defines a plurality of staple forming pockets therein at a location radially outward of the inner diametral edge; a recess formed in the anvil head, wherein the recess is defined by the inner diametral edge of the anvil plate and a rear surface of the anvil head; and a wound treatment material disposed substantially within the recess.

U.S. Patent Publication No. 2012/0241492 "TISSUE THICKNESS COMPENSATOR COMPRISING AT LEAST ONE MEDICAMENT" discloses a stapling assembly for use with a stapler, said stapling assembly comprising: an anvil comprising a plurality of forming surfaces; a compensator attached to said anvil, wherein said compensator comprises a plurality of cavities aligned with said forming surfaces; and at least one medicament positioned within each said cavity.

U.S. Pat. No. 8,821,523 "Structure for applying sprayable wound treatment material" discloses a guard for use in combination with an anastomotic surgical stapling apparatus, wherein the surgical stapling apparatus is configured and adapted to dispense staples from a staple pusher member of a body portion of the surgical stapling apparatus and to deliver wound treatment material from a stem of an anvil assembly of the surgical stapling apparatus to a target surgical site, wherein the guard comprises: a central hub defining a lumen therethrough for receiving the stem of the anvil assembly of the surgical stapling apparatus; an annular cuff supported by the central hub and extending at least substantially therearound, wherein the annular cuff is configured to be disposed radially outward of a staple line of the surgical stapling apparatus, and wherein the annular cuff defines an arcuate upper lip connected to an arcuate lower lip; and an annular flange extending radially inwardly from a radially-outermost portion of the annular cuff, the annular flange being positioned for staples to be fired therethrough.

U.S. Pat. No. 9,010,605 "Sliding sleeve for circular stapling instrument reloads" discloses a surgical stapling device for joining tissue portions, comprising: a handle assembly; an elongate body extending from the handle assembly; a cartridge assembly supported on a distal end of the elongate body, the cartridge assembly including a staple cartridge containing a plurality of surgical staples in an annular array; an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue therebetween, the head of the anvil assembly transitionable between a first condition, where a tissue contacting surface of the head is substantially perpendicular to the shaft, and a second condition, where the tissue contacting surface of the head is tilted relative to the shaft; and a sleeve member slidably disposed about the shaft of the anvil assembly, the sleeve member transitionable between a first position, where the sleeve member engages the head of the anvil assembly to secure the head in the first condition, and a second position, where the sleeve member is disengaged from the head of the anvil assembly to allow the head to transition to the second condition.

There is a need to deliver medicants in the area of the anastomotic joint for localized release to prevent ulceration and leaks, however it is difficult to create the necessary concentrations of medicants in an open area. Further, there is a need to temporary isolate anastomotic joint form the environment of the GI tract.

The known systems of isolating anastomotic joints can be complex, unreliable, and unable to fully isolate areas of resected and stapled tissue. The staple based anastomotic joining is a widely accepted practice but there is a need in improving the technology to prevent post-operative leakage of the stapled tissue seals to improve the viability of the tissue joined by staples.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage.

Tubular polymeric sleeves, optionally impregnated with a medically useful agent, are carried on the anvil and/or on the stapling head and are stapled to the anastomotic joint as the anastomosis is performed. The sleeves are then left in the lumen after the stapling and removal of the circular stapler, creating an isolating enclosure around the anastomotic joint. The sleeves are optionally releasing medicants such as antibiotic agents and/or microflora into the isolating enclosure thus treating the tissue in the areas proximal to the anastomotic joint, including stapled tissue, resected tissue, and surrounding tissue.

The present invention, in one aspect, relates to a circular surgical stapler for anastomotic joining of tissue having an anvil having a tissue facing end and an opposite distal end; the anvil having a peripheral staple bending zone and a coaxial circular knife recess on said tissue facing end; the anvil having a circumferential recess formed inside said anvil, with a circumferential entrance into said circumferential recess positioned on said tissue facing end coaxially between the staple bending zone and the circular knife recess; a cylindrical stapling head mounted on a support shaft, said stapling head containing a plurality of deployable staples in concentric arrays on a tissue facing side and a concentric knife; a moveable shaft connecting the anvil and stapling head; and an elongated hollow anvil sleeve having a flange at a proximal end thereof, said anvil sleeve open at a distal end thereof and at the proximal end thereof; said flange positioned on the tissue facing end of the anvil sleeve against said staple bending zone; and said distal end of said anvil sleeve is releasably disposed in said circumferential recess.

The present invention, in one aspect, relates to a method of establishing an anastomotic joint between tubular tissue lumens with the circular stapling instrument, the method comprising the steps of: axially positioning the anvil sleeve on the anvil; axially inserting said anvil into a first tubular tissue and closing said first tubular tissue around said anvil; axially inserting said stapling head into a second tubular tissue; connecting said anvil to said stapling head via the moveable shaft; approximating said anvil and said stapling head to compress said first and second tubular tissues between said stapling head and said anvil; firing said anastomotic stapler to form a stapled anastomotic joint between said first and second tubular tissues and simultaneously stapling said anvil sleeve to said first and second tubular tissue; withdrawing said anastomotic stapler from said first and second tubular tissues, leaving said anvil sleeve inside said first and second tubular tissues, turning and inverting said anvil sleeve outside-in; extending said anvil sleeve from said first tubular tissue into said second tubular tissue; and leaving said anvil sleeve inside said first and second tubular tissues for sufficient time for at least partial healing of said tissues at the anastomotic joint.

BRIEF DESCRIPTION OF THE FIGURES

FIGS. 2A-2C show cross-sectional views taken from FIGS. 4, 5, 6 of U.S. Pat. No. 7,776,081 entitled "Devices and methods for anastomosis".

FIGS. 4A-4F show schematic perspective and cross-sectional views of anvil sleeves of the present invention.

FIGS. 8A-8F show schematic cross-sectional views of anvils of the present invention.

FIGS. 10A, 10B and 11 show schematic cross-sectional view of stapler of the present invention in operation.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-operative leakage of the anastomosis has been shown to lead to morbidity and mortality.

Typical surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Figure 1:
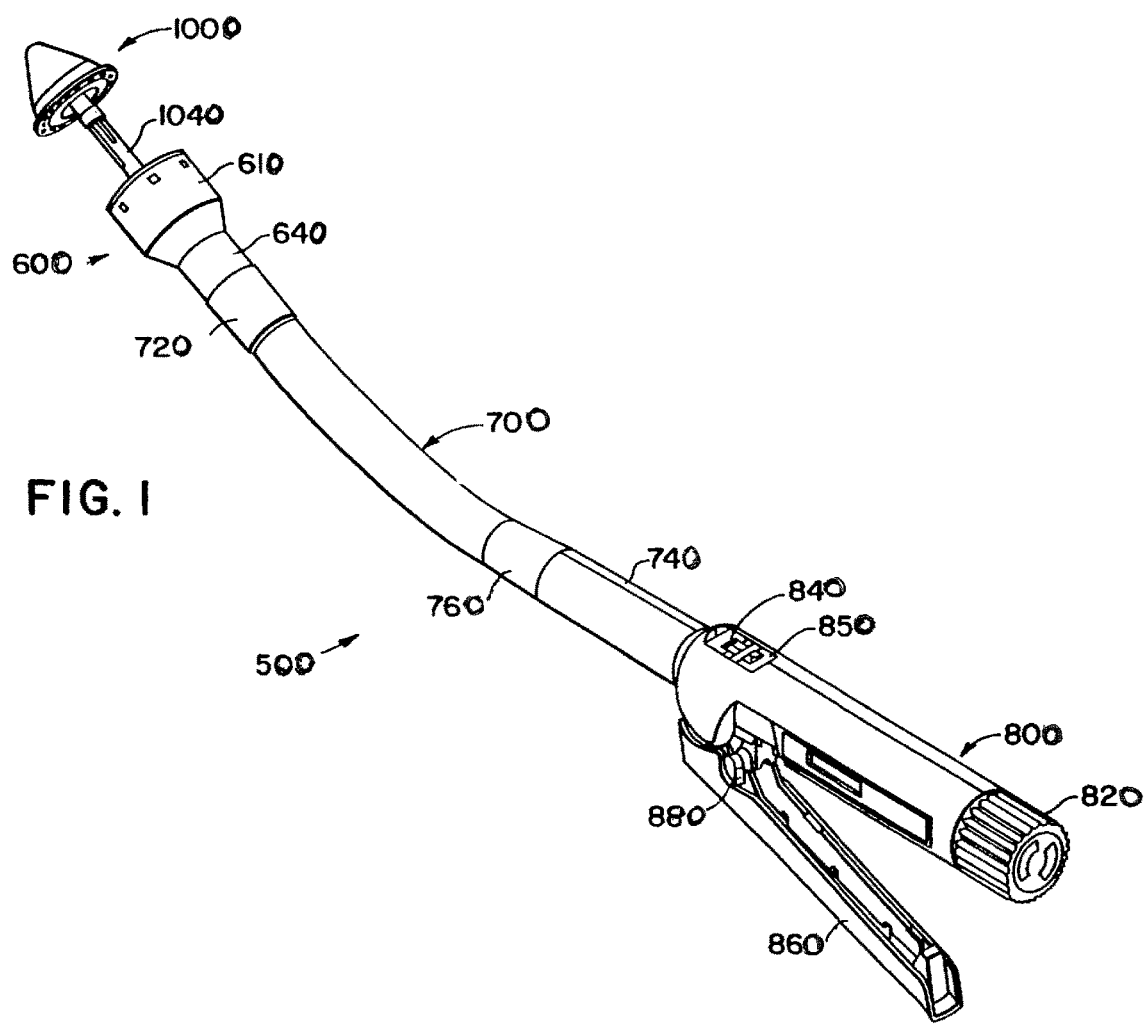
FIG. 1 shows a perspective view of a typical circular surgical stapling instrument.

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500 includes a distal stapling head assembly 600 connected by a longitudinally curved support shaft assembly 700 to a proximal actuator handle assembly 800. The stapling instrument includes an anvil assembly or anvil 1000 which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000. Other approximating means to compress adjacent sections of tissue are known to skilled artisans and can be used. An optional movable indicator 840 is visible through an optional window 850 on top of the handle assembly 800 to indicate the staple height and/or gap between the stapling head assembly 600 and anvil 1000 selected by rotation of the adjusting knob 820. The indicator 840 is movable indicating that the anvil gap is within a desired operating range of the stapling instrument 500. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000 is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jönsson, H. Jiborn, B. Zederfeldt, "Breaking strength of small intestinal anastomoses", The American Journal of Surgery, v. 145, pp. 800-803, 1983; Y.-H. Ho, M. A. T. Ashour, "Techniques for colorectal anastomosis", World Journal of Gastroenterology, 16(13), pp. 1610-1621, 2010.

Figure 3:
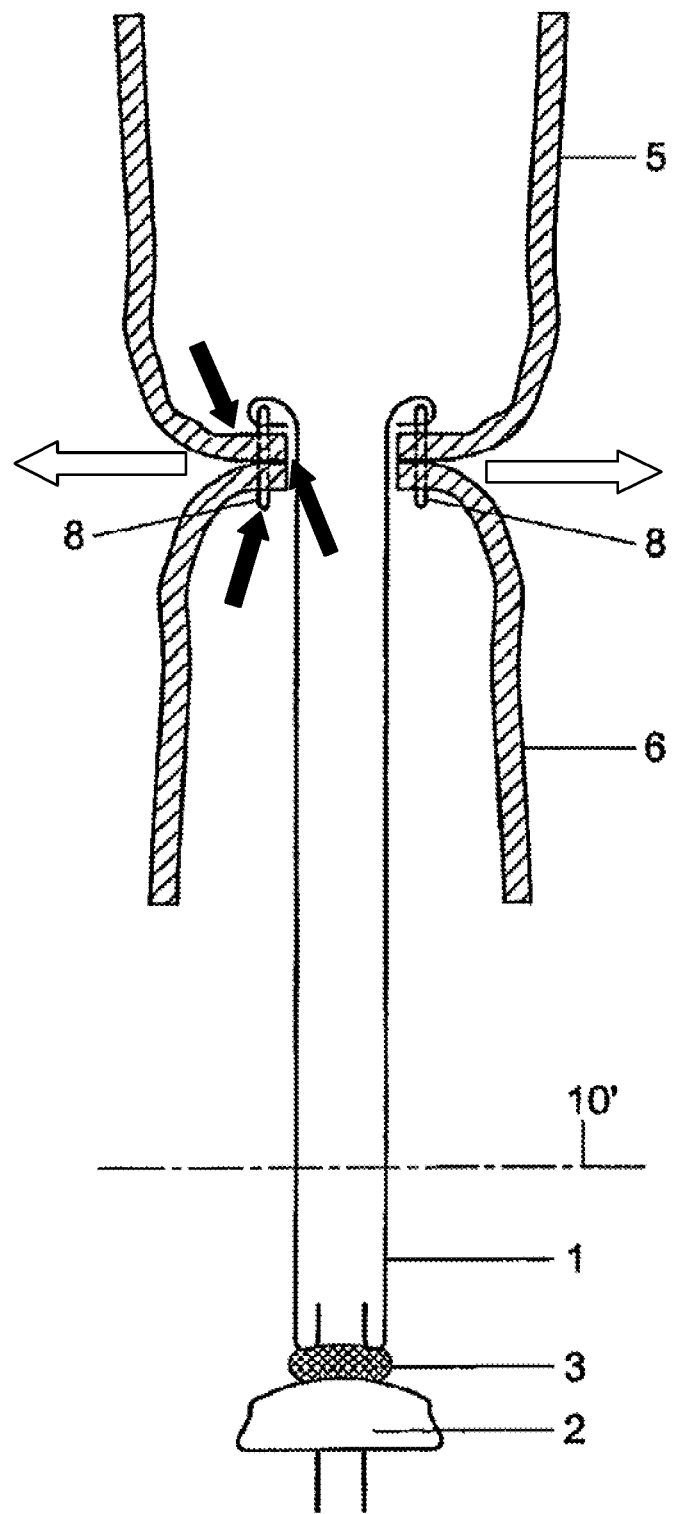
FIG. 3 shows cross-sectional view taken from FIG. 6 of U.S. Pat. No. 7,776,081 entitled "Devices and methods for anastomosis" with additional arrow indicators.

Referring now to FIGS. 2A-2C, tubular shaped colorectal drain of U.S. Pat. No. 7,776,081 is shown, whereby FIGS. 4, 5 and 6 of said patent are reproduced, showing the device stapled to the anastomotic joint. Referring now to FIG. 3, whereby FIG. 6 of said patent is again reproduced with added arrows indicating deficiencies of the device. Specifically, small dark arrows show areas that the device fails to isolate (specifically the stapled areas of tissue and cut areas of tissue) from the exposure to intestinal environment and/or microflora. Large white arrows schematically indicate that the device fails to prevent leakage if the anastomotic joint is transiently leaking.

Briefly, according to the present invention, an isolating sleeve or sleeves is/are positioned on the circular anastomotic stapler and deployed with one end of the sleeve stapled to the anastomotic joint as the staples from a circular anastomotic stapler are deployed and an anastomotic joint is established connecting two parts of a tissue lumen. As the circular anastomotic stapler is withdrawn, the sleeve or sleeves is/are released from the stapler and cover and isolate the areas of tubular tissue that were stapled together, providing additional reinforcement and particularly isolating the just stapled and just resected areas from contaminations and potential infection. Optionally, a medicant is released from the sleeve into the pocket areas formed between the sleeve and the tissue, such medicant being for instance an anti-bacterial or anti-infective agent.

Referring now to FIGS. 4A-4F, showing embodiments of the present invention, FIG. 4A shows a schematic perspective view of generally hollow, cylindrical shaped, flexible, and tubular anvil sleeve 200 of the present invention, with anvil sleeve 200 formed by wall 240 connecting distal sleeve opening 220, formed by circular edge 210, to proximal flange 235 having proximal opening 230 formed in proximal flange 235.

Referring to FIG. 4B, a schematic cross-sectional view of anvil sleeve 200 of FIG. 4A is shown. FIG. 4C shows a schematic cross-sectional view of another embodiment of anvil sleeve 200 having a reinforcing buttress 205a installed onto flange 235 on the side opposite to tissue facing side of flange 235 which is side of flange 235 facing distal sleeve opening 220. Also shown is a distal portion 213 which a portion of wall 240 which is distal to flange 235 and proximal to distal sleeve opening 220. FIG. 4D shows a schematic cross-sectional view of another embodiment of anvil sleeve 200 having a similar reinforcing buttress 205b which is installed onto tissue facing side of flange 235, which is side of flange 235 not facing distal sleeve opening 220. Buttress 205a, 205b can also prevent radial distention which can cause high tension of the tissue at the joint. Buttress can also help to spread coverage by anvil sleeve 200.

Turning now to FIG. 4E a schematic perspective view of anvil sleeve 200 is shown with proximal opening 230 formed in proximal flange 235 being smaller than the diameter of wall 240 in the proximity to flange 235, thus forming inner flange 231 extending proximal flange 235 towards center of anvil sleeve 200 between wall 240 and proximal opening 230. FIG. 4F shows a schematic cross-sectional view of the embodiment of FIG. 4E. Proximal opening 230 in the embodiments of FIGS. 4E-4F is configured to accept moveable shaft 1040.

In some embodiments, at least a portion of anvil sleeve 200 has varying mechanical properties, such as rigidity, flexibility, or thickness, along the sleeve. In one embodiment, flange 235 is thicker and less flexible than the rest of anvil sleeve 200. In some embodiments an expandable elastic ring is incorporated into circular edge 210.

Figure 5A:
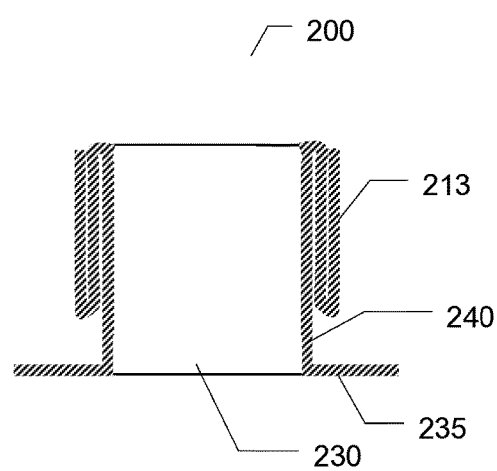
FIGS. 5A-5D show schematic cross-sectional views of anvil sleeves of the present invention.
Figure 5B:
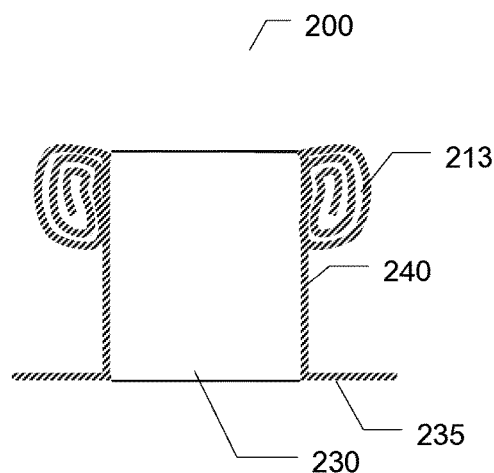
Figure 5C:
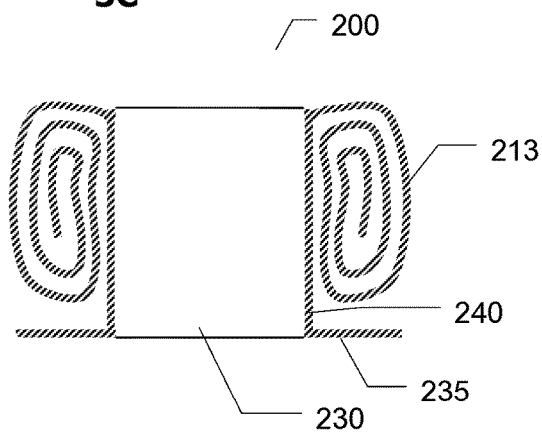
Figure 5D:
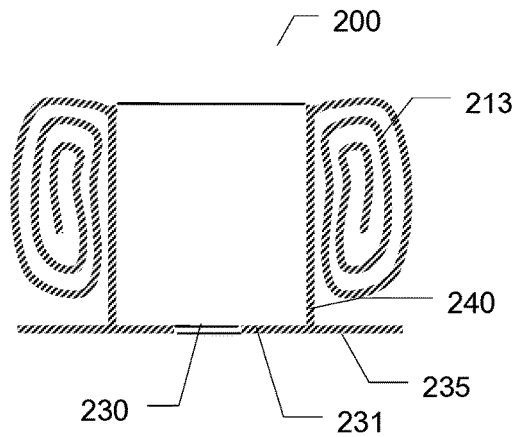

Referring now to FIGS. 5A-5D, embodiments of anvil sleeve 200 are shown in a schematic cross-sectional view with a distal portion 213 of anvil sleeve 200 inverted and folded or rolled backwards onto wall 240. FIG. 5A shows an embodiment of anvil sleeve 200 with distal portion 213 inverted and folded flat twice on outside of wall 240. Distal portion 213 can be folded once, twice (as shown), or more times. FIG. 5B shows an embodiment of anvil sleeve 200 with distal portion 213 inverted and rolled on itself on the outside of wall 240 with a space of 3-15 mm between rolled distal portion 213 and flange 235. FIG. 5C shows an embodiment of anvil sleeve 200 with distal portion 213 inverted and rolled on itself on the outside of wall 240 with a space of less than 3 mm, such as 0, 1, 2, 2.5 mm between rolled distal portion 213 and flange 235. FIG. 5D shows an embodiment of anvil sleeve 200 corresponding to embodiments of FIGS. 4E, 4F having inner flange 231 with distal portion 213 inverted and rolled on itself on the outside of wall 240.

Figure 6A:
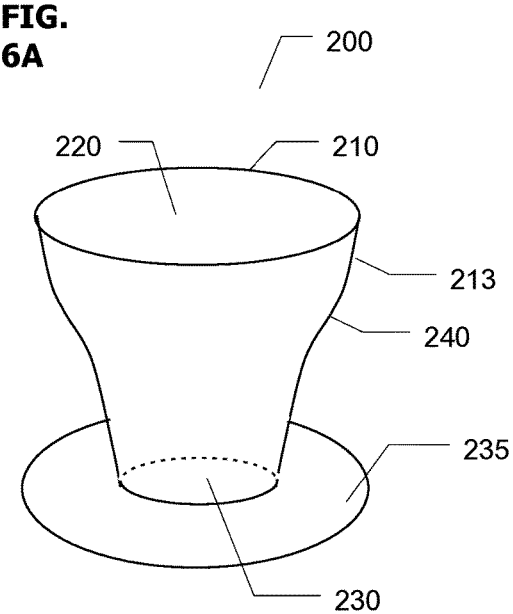
FIGS. 6A-6G show schematic perspective and cross-sectional views of anvil sleeves of the present invention.
Figure 6B:
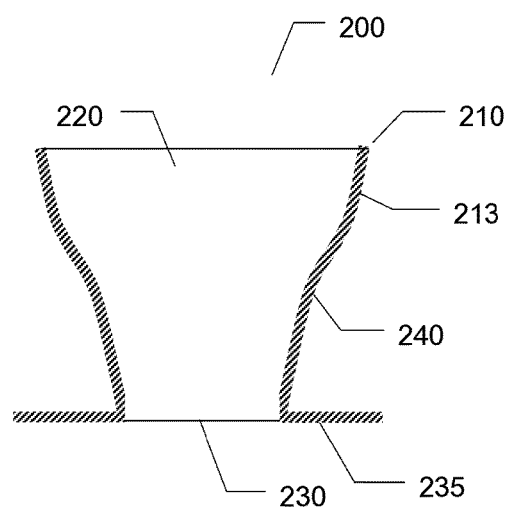

Turning now to FIG. 6A, a schematic perspective view of another embodiment of anvil sleeve 200 having a frustoconical shape with narrower hollow portion at proximal flange 235 and wider hollow portion at distal sleeve opening 220 or at circular edge 210. FIG. 6B shows a schematic cross-sectional view of the embodiment of anvil sleeve 200 shown in FIG. 6A. Also shown is a distal portion 213 which a portion of wall 240 which is distal to flange 235 and proximal to distal sleeve opening 220.

Figure 6C:
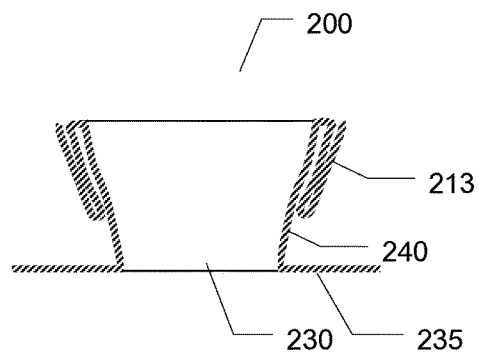
Figure 6D:
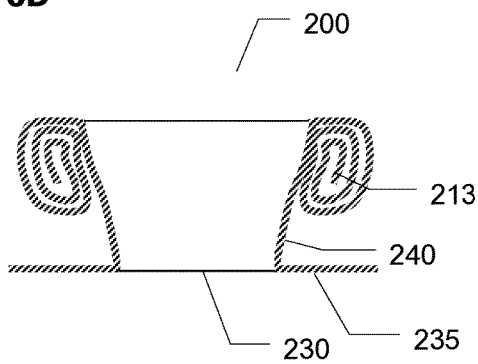

Turning now to FIG. 6C, a schematic cross-sectional view of an embodiment of anvil sleeve 200 of the present invention is shown, with distal portion 213 inverted and folded flat twice on outside of wall 240. Distal portion 213 can be folded once, twice (as shown), or more times. FIG. 6D shows an embodiment of anvil sleeve 200 with distal portion 213 inverted and rolled on itself on the outside of wall 240 with a space of 0-15 mm between rolled distal portion 213 and flange 235.

Figure 6E:
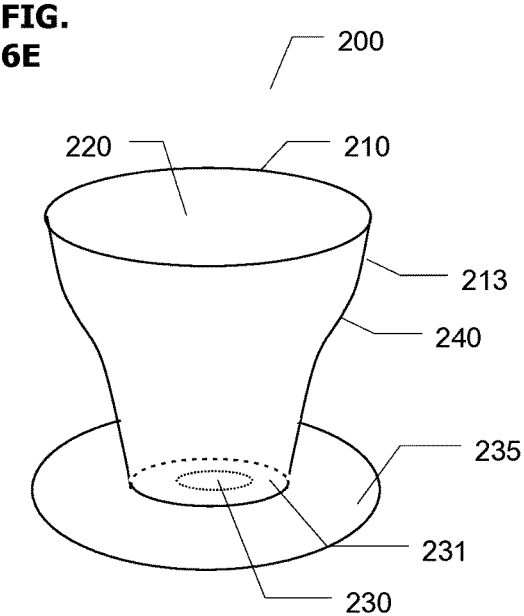
Figure 6F:
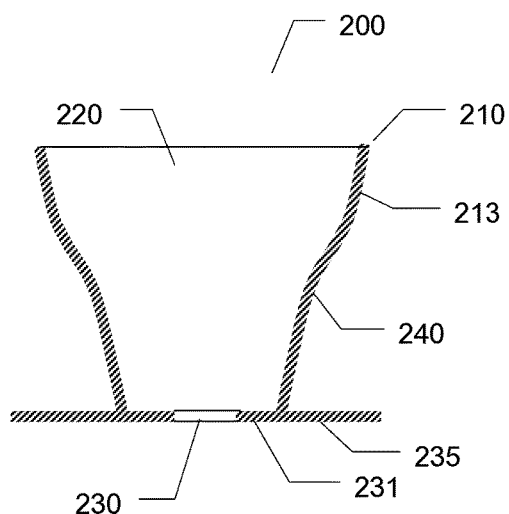
Figure 6G:
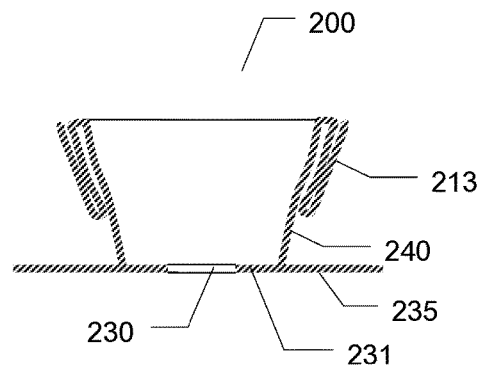

Turning now to FIG. 6E, a schematic perspective view of an embodiment of anvil sleeve 200 having a frustoconical shape with proximal opening 230 formed in proximal flange 235 being smaller than the diameter of wall 240 in the proximity to flange 235, thus forming inner flange 231 extending proximal flange 235 between wall 240 and proximal opening 230. FIG. 6F shows a schematic cross-sectional view of the embodiment of FIG. 6E. FIG. 6G, shows a schematic cross-sectional view of an embodiment of anvil sleeve 200 of the present invention inner flange 231, with distal portion 213 inverted and folded flat twice on outside of wall 240. Proximal opening 230 in the embodiments of FIGS. 6E-6F is configured to accept moveable shaft 1040.

Figure 7:
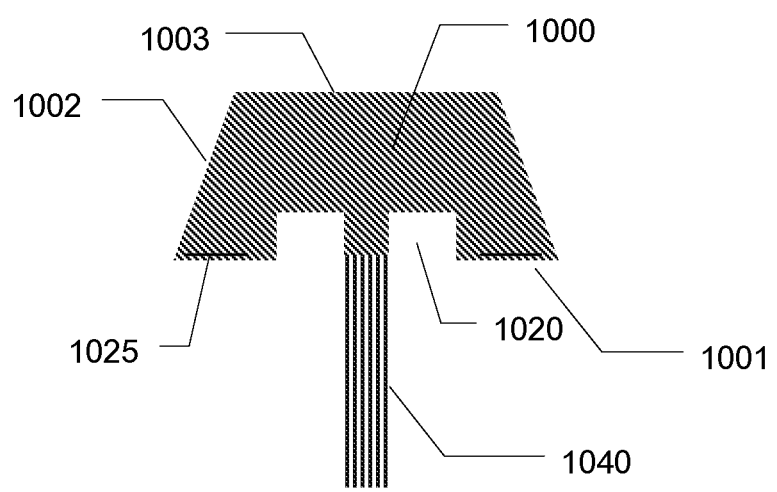
FIG. 7 shows schematic cross-sectional views of anvil known in the art.

Turning now to FIG. 7, a schematic cross-sectional view of anvil 1000 is shown as known in the art. Anvil 1000 is shown having distal end or upper portion 1003, sidewall 1002, tissue facing end or staples facing surface 1001, staple bending zone 1025 at a periphery of staples facing surface 1001 opposing staples 110 rows (not shown); moveable shaft 1040 connected to anvil 1000, and circular or concentric knife abutting zone or circular knife recess 1020.

Turning now to FIGS. 8A-8F, schematic cross-sectional views of anvil 1000 of present invention are shown. FIG. 8A shows an embodiment of anvil 1000 having an enclosed chamber or circumferential recess 1030a inside, with circumferential entrance 1031 into circumferential recess 1030a. Circumferential entrance 1031 is positioned on tissue facing end or staples facing surface 1001. Circumferential entrance 1031 is positioned coaxially around circular knife abutting zone or circular knife recess 1020; Circumferential entrance 1031 is in turn coaxially surrounded by staple bending zone 1025 located at the periphery of staples facing surface 1001. Circumferential entrance 1031 is configured not to overlap with staple bending zone 1025 or with circular knife abutting zone or circular knife recess 1020, with circular separation wall 1021 coaxially positioned between circumferential entrance 1031 and circular knife recess 1020.

FIG. 8B shows an embodiment similar to one shown in FIG. 8A, but having wider and expanded circumferential recess 1030b inside anvil 1000, with the same narrow circumferential entrance 1031 into circumferential recess 1030a. The expansion of circumferential recess 1030b inside anvil 1000 can be in any direction as shown, i.e. directed towards both the periphery and center of anvil 1000.

FIG. 8C shows an embodiment similar to one shown in FIG. 8A, but having wider and expanded circumferential recess 1030c inside anvil 1000, with the same narrow circumferential entrance 1031 into circumferential recess 1030c. The expansion of circumferential recess 1030c inside anvil 1000 can be in any direction but in this embodiment it is directed mostly towards center of anvil 1000.

FIG. 8F shows an embodiment similar to one shown in FIG. 8A, but having wider and expanded circumferential recess 1030d inside anvil 1000, with the same narrow circumferential entrance 1031 into circumferential recess 1030d. The expansion of circumferential recess 1030d inside anvil 1000 can be in any direction but in this embodiment it is directed mostly towards periphery of anvil 1000.

FIG. 8E shows an embodiment similar to one shown in FIG. 8A, but having circumferential recess 1030e without circular separation wall 1021 between circumferential entrance 1031 and or circumferential recess 1030e and circular knife recess 1020.

FIG. 8D shows an embodiment similar to one shown in FIG. 8E, but having circumferential recess 1030f merged with circular knife recess 1020.

Figure 9A:
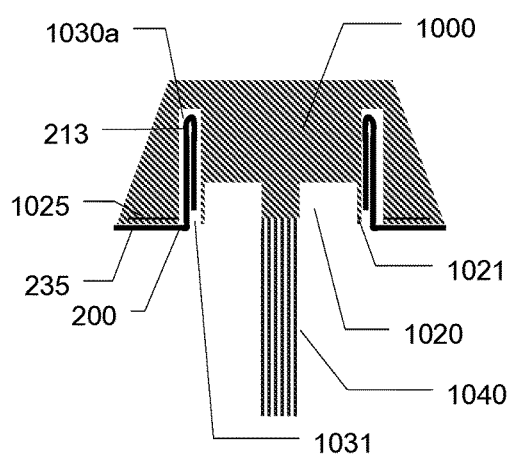
FIGS. 9A-9D show schematic cross-sectional views of anvil sleeves and anvils of the present invention.

Turning now to FIGS. 9A-9D, schematic cross-sectional views of anvil 1000 of present invention are shown with anvil sleeve 200 installed. FIG. 9A shows an embodiment of anvil 1000 similar to the embodiment of FIG. 8A with anvil sleeve 200 similar to the embodiments of FIG. 5A or 6C installed. Flange 235 is abutting periphery of staples facing surface 1001 and installed against staple bending zone 1025. The whole wall 240 or at least a portion of wall 240 of anvil sleeve 200, such as distal portion 213, is inserted into and packaged into circumferential recess 1030a, being inserted through circumferential entrance 1031 and folded on itself inside circumferential recess 1030a.

Figure 9B:
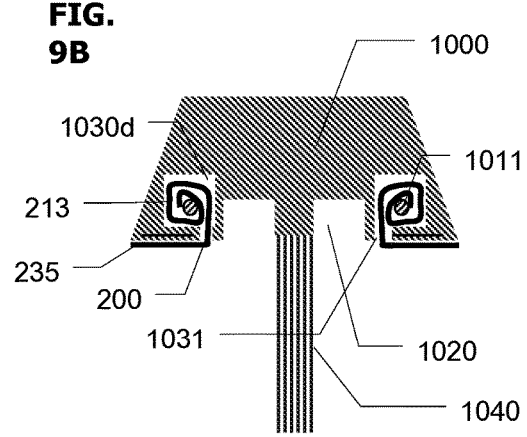

FIG. 9B shows an embodiment of anvil 1000 similar to the embodiment of FIG. 8B or 8D with anvil sleeve 200 similar to the embodiments of FIGS. 5B-C or 6D installed. Flange 235 is abutting periphery of staples facing surface 1001 and installed against staple bending zone 1025. The whole wall 240 or at least a portion of wall 240 of anvil sleeve 200, such as distal portion 213, is inserted into and packaged into circumferential recess 1030d, being inserted through circumferential entrance 1031 and rolled on itself inside circumferential recess 1030d.

FIG. 9B also shows an optional retaining ring 1011 installed inside circumferential recess 1030d. Retainer ring 1011 configured to loosely fit into circumferential recess 1030d. Retainer ring 1011 can be made of any material, such as metal, polymer, etc. Retainer ring 1011 can be elastic, rigid, or semi-rigid. As shown in FIG. 9B, distal portion 213 can be optionally rolled around retainer ring 1011. Alternatively (not shown) distal portion 213 can be rolled on itself above retainer ring 1011.

Figure 9C:
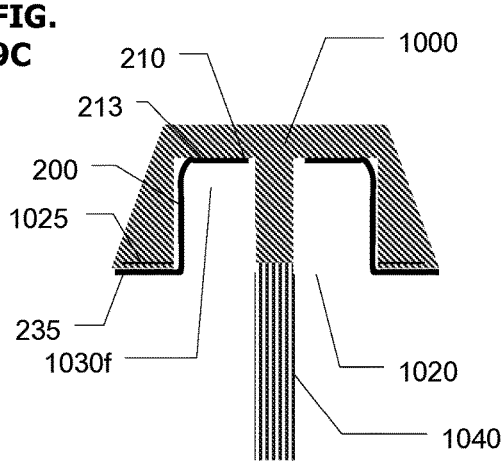

FIG. 9C shows an embodiment of anvil 1000 similar to the embodiment of FIG. 8F with anvil sleeve 200 similar to the embodiments of FIG. 4B or 6B installed. Flange 235 is abutting periphery of staples facing surface 1001 and installed against staple bending zone 1025. The whole wall 240 or at least a portion of wall 240 of anvil sleeve 200, such as distal portion 213, is inserted into and packaged into circumferential recess 1030f, while positioned to avoid any interference with circular knife moving against and within circular knife recess 1020.

Figure 9D:
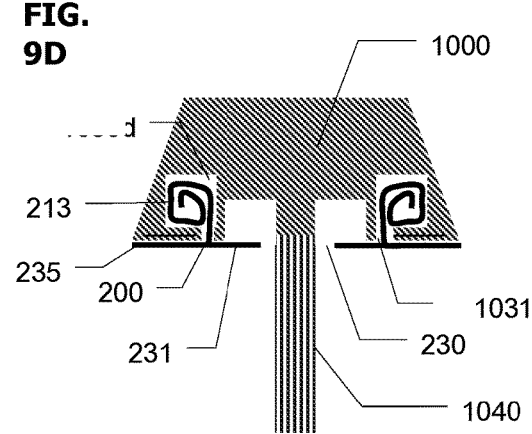

FIG. 9D shows an embodiment of anvil 1000 and anvil sleeve 200 similar to the embodiment of 9B, but with anvil sleeve 200 having inner flange 231.

According to the embodiments of the present invention, in all embodiments, anvil sleeves 200 as shown in FIGS. 4, 5, 6 are installed onto anvils 1000 as shown in FIG. 8, with flange 235 abutting periphery of staples facing surface 1001 and opposing staples 110 rows and installed against staple bending zone 1025. The whole wall 240 or at least a portion of wall 240 of anvil sleeve 200, such as distal portion 213, is inserted into and packaged into circumferential recess 1030, optionally inserted through circumferential entrance 1031 and optionally folded on itself or rolled on itself inside circumferential recess 1030. In all embodiments, excluding embodiments having inner flange 231, anvil sleeves 200 are configured and positioned to avoid any interference with circular or concentric knife moving against and within circular knife recess 1020. In embodiments having inner flange 231, inner flange 231 is cut by the action of concentric knife during stapling.

According to one embodiment of the present invention, a first portion of anvil sleeve 200, comprising flange 235 is mounted onto staple bending zone 1025; a second portion of anvil sleeve 200 comprising distal portion 213, is releasably stored in circumferential recess 1030; and a third portion of anvil sleeve 200 comprising a part of wall 240 intermediate between flange 235 and distal portion 213 passes through circumferential entrance 1031.

As shown above, anvil sleeve 200, which can be made of polymeric, flexible, and at least partially elastic materials, is configured to have at least a portion of wall 240 to releasably fit inside anvil 1000 with anvil 1000 at least partially enveloping anvil sleeve 200 wall 240 inside circumferential recess 1030.

In one embodiment, walls 240 of anvil sleeve 200 contain multiple apertures, pores or perforations (not shown), having size from about 0.1 mm to about 3 mm, such as 0.25 mm, 0.5 mm, 1 mm. In one embodiment, only distal portion 213 has multiple apertures, pores or perforations (not shown). In one embodiment, apertures are round, square, triangular, or similar. In another embodiment the apertures comprise elongated cuts with length to width ratio from 5 to 150, such as for width of the cut 0.1 mm, the length of the cut being 10 mm.

Referring now to FIG. 10A, a schematic cross-sectional partial view of a portion of circular stapler performing anastomotic joining of tubular tissues T1 and T2 is presented. Anvil 1000 is shown disposed within tubular tissue T1 and connected to stapling head 600 via moveable shaft 1040. Stapling head 600 is shown disposed within tubular tissue T2 and supported on support shaft assembly 700. For simplification, the mechanism of staples deployment and mechanism of deploying tissue cutting circular or concentric knife 601 are not shown. FIG. 10 shows anvil 1000 and stapling head 600 approximated, compressing tissue T1 and T2 between them. Flange 235 of anvil sleeve 200 is disposed between stapling head 600 and anvil 1000, with flange 235 on tissue facing side of anvil sleeve 200.

FIG. 10 shows embodiment of anvil sleeve 200 of FIGS. 5B, 5C, 6D, mounted on embodiment of anvil 1000 similar to embodiment of FIG. 8C. Any other embodiments of anvil sleeve 200 and anvil 1000 of the present invention can be substituted for embodiments shown in FIG. 10 and infra.

Referring now to FIG. 10B, an embodiment of the present invention similar to one shown in FIG. 10A is presented, but with anvil sleeve 200 having inner flange 231. During stapling, inner flange 231 is cut by the action of concentric knife 601.

Figure 11:
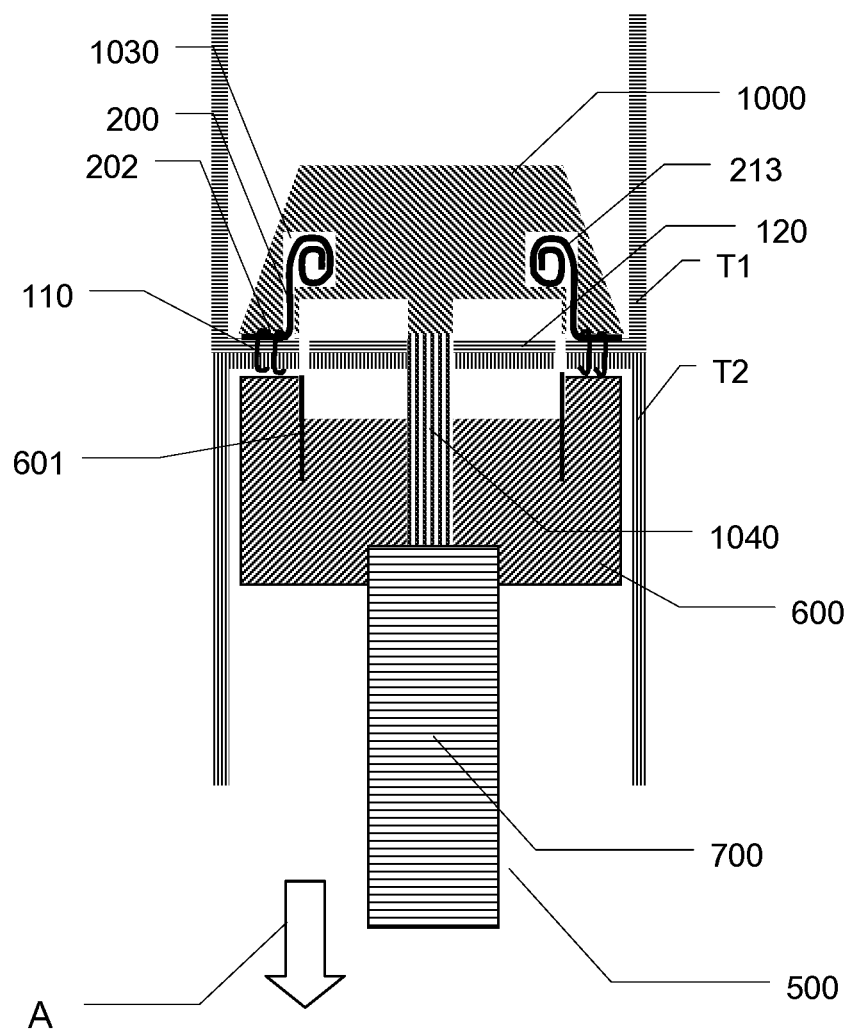

Referring now to FIG. 11, the configuration of embodiment of FIG. 10 is shown after actuating stapling instrument 500, i.e. after staples 110 fired thus establishing a stapled joint between tissues T1 and T2 with staples 110 concentrically arranged in one or more concentric rows around tissue donut or cut-out 120 which is formed by deploying and then retracting tissue cutting circular or concentric knife 601. Areas 202 of anvil sleeve 200 which are opposing staples 110 rows and corresponding to flange 235, are stapled to tissues T1 and T2.

After deploying staples 110 and cutting out tissue cutout 120 thus establishing the anastomotic joint, with anvil sleeve 200 stapled to tissues T1 and T2, in the area corresponding to flange 235, circular stapler 500 is withdrawn in the direction of arrow A. As anvil 1000 moves past staples 110 in the direction of arrow A, with anvil sleeve proximal end or flange 235 immobilized on tissue by staples 110, anvil sleeve 200 is turned outside-in and inverted with distal portion 213 released from circumferential recess 1030.

For embodiments of anvil sleeve 200 having inner flange 231, as was shown in FIG. 10B, during stapling, inner flange 231 is cut from anvil sleeve 200 by the action of concentric knife 601. Inner flange 231 is thus separated from anvil sleeve 200 and remains between anvil 1000 and stapling head 600 even after removal of circular stapler 500 form tubular tissues T1 and T2.

Figure 12:
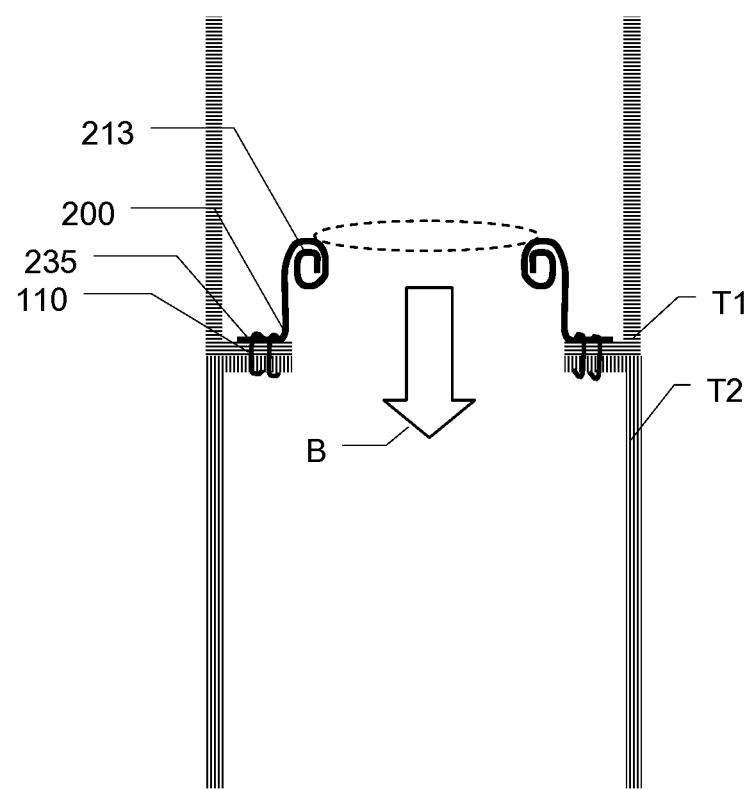
FIGS. 12 and 13 show schematic cross-sectional view of anvil sleeve of the present invention in operation.

Referring now to FIG. 12, a schematic cross-sectional view of configuration shown in FIG. 11 is presented, omitting circular stapler 500. Arrow B shows the direction where anvil sleeve 200 distal end is pulled by anvil 1000 (not shown). Anvil sleeve 200 thus is turned outside-in and inverted while released into tubular tissue T2 from circumferential recess 1030.

Figure 13:
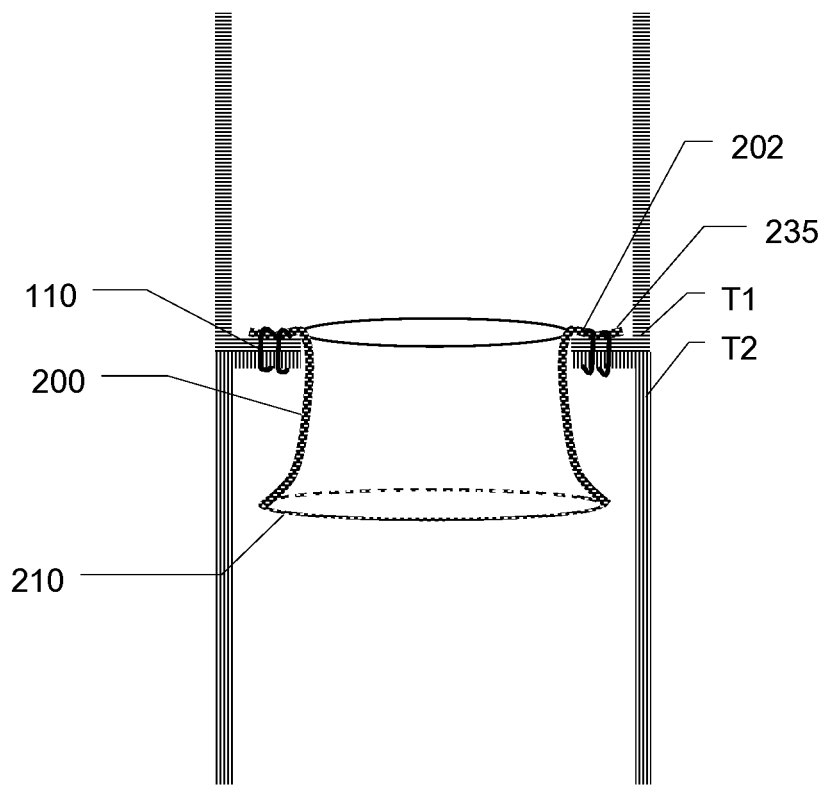

Referring now to FIG. 13, a schematic cross-sectional view of configuration after removal of circular stapler 500 and deployment of anvil sleeve 200 around and onto anastomotically joined tissue lumens T1 and T2 is shown. Anvil sleeve 200 is stapled to tissues T1 and T2 within tissue lumen T1 and then inverted/turned outside-in, passes over area of tissues T1 and T2 stapled by staples 110, extending from tissue lumen T1 into tissue lumen T2, and then completes covering the areas of cut and stapled tissues T1 and T2.

Advantageously, areas of cut and stapled tissues T1 and T2 are beneficially protected by anvil sleeve 200 which extends above and below the immediate vicinity of the established anastomotic joint, enabling isolation and protection of vulnerable tissues around the anastomotic joint, which can be subject to ulceration and leaks.

According to one embodiment of the present invention, the sequence of using anvil sleeve 200 of the present invention while establishing an anastomotic joint and isolating and protecting the anastomotic joint is as follows:

a) Axially positioning anvil sleeve 200 on anvil 1000 with flange 235 abutting periphery of staples facing surface 1001 and installed against staple bending zone 1025, with at least a portion of wall 240 of anvil sleeve 200 inserted into and packaged into circumferential recess 1030;

b) Axially inserting anvil 1000 into tubular tissue T1 and closing tissue T1 around anvil 1000;

c) Axially inserting stapling head 600 into tubular tissue T2;

d) Connecting anvil 1000 to stapling head 600 via anvil shaft 1040;

e) Approximating anvil 1000 and stapling head 600 and compressing tubular tissues T1 and T2 between stapling head 600 and anvil 1000;

f) Firing anastomotic stapler 500 and establishing stapled anastomotic joint between tissues T1 and T2 and simultaneously stapling anvil sleeve 200 to tissues T1 and T2 in the area of flange 235;

g) Withdrawing anastomotic stapler 500 from tissue lumens T1 and T2 and leaving anvil sleeve 200 inside tissue lumens T1 and T2, while anvil sleeve 200 is released from circumferential recess 1030, turned outside-in and inverted and deployed inside tissue T2;

h) Allowing anvil sleeve 200 to extend from its proximal end and flange 235 stapled to tissue T1 over the resected/stapled areas of tissues T1 and T2 and into tissue lumen T2 where the opposite distal end of anvil sleeve 200 is then positioned; and i) Leaving anvil sleeve 200 inside tissue lumens T1 and T2 until at least partial healing of tissues at the established anastomotic joint.

Complete steps of anastomotic surgical procedures, e.g. application of purse string sutures are not listed above, but will be known to skilled artisans. Additional steps after the installation of anvil sleeve 200 include:

j) Optionally releasing medicants accelerating healing and/or preventing infection and/or managing inflammation from anvil sleeve 200;

k) Optionally releasing a specialized microflora from anvil sleeve 200; and l) Allowing the anvil sleeve 200 to pass through the GI tract out of the body after a period of from 3 days to about 8 weeks, more preferably 1 week, 2 weeks, 3 weeks, 4 weeks, or 6 weeks.

In certain embodiments anvil sleeve 200 is made of non-resorbable polymers or composites, preferably from polymeric and elastomeric materials. In one embodiment, sleeves are made of materials with low elasticity, low elastomeric properties materials, or are made of elastomeric compressible/expandable materials, and are made of at least partially resorbable or erodible/soluble materials. Sleeves 200 are excreted as the stapled areas of tissues T1 and T2 eventually undergo necrotic transformation and die off.

In certain embodiments anvil sleeve 200 is made of at least partially resorbable or erodible/soluble materials which are known to a skilled artisan, with time to at least partially dissolve or resorb from about 3 days to about 30 days in the gastro-intestinal (GI) tract, such as 1 week, 2 weeks, 3 weeks, or 4 weeks, most preferably 2-4 weeks. In some embodiments, sleeves 200 walls 240 are made from non-resorbable polymers or composites.

According to the present invention, in addition to shielding/isolating the areas of resected and stapled tissue from GI environments, there is provided an optional release of medicants accelerating healing and/or preventing infection from anvil sleeve 200. Further, a specialized microflora can be released from anvil sleeve 200.

According to the present invention, anvil sleeve 200 is optionally at least partially coated or impregnated with releasable antimicrobial agents. All portions of anvil sleeve 200 can be treated with such agents, or specific portions which are in contact with areas of tissues T1 and T2 or specific portions which are not in contact with areas of tissues T1 and T2 can be coated or impregnated with releasable medically useful agents, such as antimicrobial agents. Advantageously, anvil sleeve 200 shields or isolates areas of stapled and cut tissue from the GI environment and enables establishment of higher sustained concentration of anti-microbial agents or other medicants, such as specific microflora, in the immediate vicinity of these areas of tissue. Such treatment is thought to minimize formation of tissue ulcerations and other defects and decrease the occurrence of anastomotic leaks.

Alternatively, or in addition to the above, agents that reduce/manage inflammation can be coated onto and/or impregnated into the sleeve.

Thickness of sleeves 200 walls 240, is from about 20 microns to about 2 mm, more preferably from 50 microns to 1 mm, such as 50, 100, 200, 300, 500 microns.

The length of anvil sleeve 200 is configured to enable sleeve 200 to be turned outside-in and extend from stapled areas of tissue T1 to below stapled area of tissue T2, but still remain fully within GI tract. In some embodiments, the length of sleeve 200 is from about 5 mm to about 75 mm, more preferably 10 mm to 50 mm, such as 10, 15, 20, 25, 30, 40, 50 mm.

In some embodiments there are apertures or micro-apertures (not shown) formed in anvil sleeve 200.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A circular stapling instrument comprising:
a) an anvil having a tissue facing end and an opposite distal end;
   the anvil having a peripheral staple bending zone and a coaxial circular knife recess on said tissue facing end;
   the anvil having a circumferential recess formed inside said anvil, with a circumferential entrance into said circumferential recess positioned on said tissue facing end coaxially between the staple bending zone and the circular knife recess;
b) a cylindrical stapling head mounted on a support shaft, said stapling head containing a concentric knife and a plurality of deployable staples in concentric arrays on a tissue facing side of said stapling head;
c) a moveable shaft connecting the anvil and stapling head; and
d) an elongated hollow anvil sleeve having a flange at a proximal end thereof,
   said anvil sleeve open at a distal end thereof and at the proximal end thereof;
   said flange positioned on the tissue facing end of the anvil against said staple bending zone;
   wherein said distal end of said anvil sleeve is releasably disposed in said circumferential recess,
   wherein a circular separation wall is formed on said tissue facing end of said anvil coaxially between the circumferential entrance and the circular knife recess.

2. The circular stapling instrument of claim 1, wherein the circumferential entrance is configured not to overlap with the staple bending zone.

3. The circular stapling instrument of claim 1, wherein the circumferential entrance is configured not to overlap with the circular knife recess.

4. The circular stapling instrument of claim 1, wherein said anvil sleeve is tubular or frustoconical.

5. The circular stapling instrument of claim 1, wherein said anvil sleeve, said circumferential recess, and said circumferential entrance are configured to avoid any interference and any contact of the anvil sleeve with the concentric knife moving against and within circular knife recess.

6. The circular stapling instrument of claim 1, wherein said anvil sleeve, said circumferential recess, and said circumferential entrance are configured to avoid any interference and any contact of the anvil sleeve with the concentric knife before, during, and after stapling with said circular stapling instrument.

7. The circular stapling instrument of claim 1, wherein said anvil sleeve further comprises an inner flange extending the flange towards center of said anvil sleeve.

8. The circular stapling instrument of claim 7, wherein said inner flange is cut by said concentric knife during stapling with said circular stapling instrument.

9. The circular stapling instrument of claim 1, wherein a portion of the anvil sleeve intermediate between the flange and the distal end of said anvil sleeve passes through the circumferential entrance.

10. The circular stapling instrument of claim 1, wherein said anvil sleeve is folded on itself or rolled on itself or inverted or turned outside-in or turned inside-out at said distal end of said anvil sleeve.

11. The circular stapling instrument of claim 1, wherein said anvil sleeve further comprises a buttress disposed on the flange.

12. The circular stapling instrument of claim 1, wherein said anvil sleeve has multiple perforations.

13. The circular stapling instrument of claim 1, wherein said anvil sleeve has multiple perforations in the distal end thereof.

14. The circular stapling instrument of claim 1, wherein at least a portion of said anvil sleeve is erodible, dissolvable, or resorbable in a mammalian gastrointestinal tract over a period ranging from 1 to 8 weeks.

15. The circular stapling instrument of claim 1, wherein said anvil sleeve is at least partially coated or impregnated with a releasable anti-bacterial, anti-microbial, anti-infective agent, bacterial culture, or combinations thereof.

16. The circular stapling instrument of claim 1, wherein at least a portion of said anvil sleeve has varying mechanical properties along the sleeve.

17. The circular stapling instrument of claim 1, wherein the flange is thicker and less flexible than the rest of said sleeve.

18. The circular stapling instrument of claim 1, wherein an expandable elastic ring is incorporated into said distal end of said anvil sleeve.

19. A method of establishing an anastomotic joint between tubular tissue lumens with the circular stapling instrument of claim 1, the method comprising the steps of:
- a. axially positioning the anvil sleeve on the anvil; axially inserting said anvil into a first tubular tissue and closing said first tubular tissue around said anvil;
- b. axially inserting said stapling head into a second tubular tissue;
- c. connecting said anvil to said stapling head via the moveable shaft;
- d. approximating said anvil and said stapling head to compress said first and second tubular tissues between said stapling head and said anvil;
- e. firing said anastomotic stapler to form a stapled anastomotic joint between said first and second tubular tissues and simultaneously stapling said anvil sleeve to said first and second tubular tissue;
- f. withdrawing said anastomotic stapler from said first and second tubular tissues, leaving said anvil sleeve inside said first and second tubular tissues,
- g. turning and inverting said anvil sleeve outside-in;
- h. extending said anvil sleeve from said first tubular tissue into said second tubular tissue; and
- i. leaving said anvil sleeve inside said first and second tubular tissues for sufficient time for at least partial healing of said tissues at the anastomotic joint.

* * * * *